(12) United States Patent
Lang

(10) Patent No.: US 7,050,534 B2
(45) Date of Patent: *May 23, 2006

(54) METHODS AND DEVICES FOR QUANTITATIVE ANALYSIS OF X-RAY IMAGES

(75) Inventor: Philipp Lang, Lexington, MA (US)

(73) Assignee: Imaging Therapeutics, Inc., Foster City, CA (US)

( * ) Notice: Subject to any disclaimer, the term of this patent is extended or adjusted under 35 U.S.C. 154(b) by 29 days.

This patent is subject to a terminal disclaimer.

(21) Appl. No.: 10/225,363

(22) Filed: Aug. 20, 2002

(65) Prior Publication Data

US 2003/0063704 A1  Apr. 3, 2003

Related U.S. Application Data

(63) Continuation-in-part of application No. 10/086,653, filed on Feb. 27, 2002, which is a continuation-in-part of application No. 09/942,528, filed on Aug. 29, 2001.

(60) Provisional application No. 60/228,591, filed on Aug. 29, 2000.

(51) Int. Cl.
*G01B 15/02* (2006.01)

(52) U.S. Cl. .......................... 378/54; 378/56

(58) Field of Classification Search .............. 378/18, 378/53, 54, 56, 207
See application file for complete search history.

(56) References Cited

U.S. PATENT DOCUMENTS

| | | | | |
|---|---|---|---|---|
| 4,251,732 A | | 2/1981 | Fried ............................ 378/170 |
| 4,400,827 A | * | 8/1983 | Spears ......................... 378/207 |
| 4,782,502 A | | 11/1988 | Shulz .......................... 378/18 |
| 4,922,915 A | | 5/1990 | Arnold ......................... 382/128 |
| 4,985,906 A | | 1/1991 | Arnold ......................... 378/18 |
| 5,001,738 A | | 3/1991 | Brooks ......................... 378/170 |
| 5,122,664 A | | 6/1992 | Ito et al. |
| 5,187,731 A | | 2/1993 | Shimura |
| 5,222,021 A | | 6/1993 | Feldman et al. .............. 378/18 |
| 5,235,628 A | | 8/1993 | Kalender ..................... 378/207 |
| 5,335,260 A | * | 8/1994 | Arnold ......................... 378/207 |
| 5,493,601 A | | 2/1996 | Fivez et al. .................. 378/207 |
| 5,565,678 A | * | 10/1996 | Manian ........................ 428/690 |
| 5,687,210 A | * | 11/1997 | Maitrejean et al. ............ 378/57 |
| 5,769,072 A | | 6/1998 | Olsson et al. ............. 128/205.13 |
| 5,852,647 A | * | 12/1998 | Schick et al. .................. 378/53 |
| 5,917,877 A | * | 6/1999 | Chiabrera et al. ............ 378/207 |
| 6,064,716 A | | 5/2000 | Siffert et al. |
| 6,246,745 B1 | | 6/2001 | Bi et al. ........................ 378/54 |
| 6,248,063 B1 | | 6/2001 | Barnhill et al. .............. 600/300 |
| 6,302,582 B1 | | 10/2001 | Nord et al. ................... 378/207 |
| 6,320,931 B1 | | 11/2001 | Arnold et al. ................. 378/56 |
| 6,377,653 B1 | * | 4/2002 | Lee et al. ...................... 378/54 |

(Continued)

FOREIGN PATENT DOCUMENTS

EP  0 678 191  10/1995

(Continued)

OTHER PUBLICATIONS

Klose (1998) "Teleradiology—A Model for Remote Consultation", *Electromedica*, 66(1): 37-41.

(Continued)

*Primary Examiner*—Courtney Thomas
(74) *Attorney, Agent, or Firm*—Kenyon & Kenyon LLP

(57) ABSTRACT

The present invention relates to network enabled analysis of x-ray images. Also described are devices comprising calibration phantoms; methods of using these devices; methods of formulating databases containing information regarding x-ray images; the databases themselves; and methods of manipulating the information and databases.

37 Claims, 8 Drawing Sheets

U.S. PATENT DOCUMENTS

| | | | |
|---|---|---|---|
| 6,811,310 B1 * | 11/2004 | Lang et al. | 378/169 |
| 6,904,123 B1 * | 6/2005 | Lang | 378/54 |
| 2002/0196966 A1 | 12/2002 | Jiang et al. | |

FOREIGN PATENT DOCUMENTS

| | | |
|---|---|---|
| EP | 0797952 A1 | 10/1997 |
| WO | WO 99/08597 | 2/1999 |
| WO | WO 99/45845 | 9/1999 |

OTHER PUBLICATIONS

Ouyang et al (1998) "Morphometric Texture Analysis of Spinal Trabecular Bone Structure Assessed Using Orthogonal Radiographic Projections", *Med. Phys.*, 25(10): 2037-2045.

Cann, "Quantitative CT for Determination of Bone Mineral Density: A Review," *Radiology 166*:509-522 (1988).

Eastell et al., "Treatment of postmenopausal Osteoporosis," *New Engl. J. of Med. 338* :736-746 (1998).

Gluer et al., "Peripheral Measurement Techniques for the Assessment of Osteoporosis," *Semin Nucl. Med.* 27:229-247 (1997).

Patel et al., "Radiation Dose to the Patient and Operator from a Peripheral Dual X-Ray Absorptiometry System," *Journal of Clinical Densitometry* 2(4):397-401 (1999).

Richard Barker, "*Case Method: Entity Relationship Modeling*" (*Computer Aided Systems Engineering*), 1990, Addison-Wesley Pub. Co., publisher.

R. Jacobs et al., "*Long-term Bone Mass Evaluation of Mandible and Lumbar Spine in a Group of Women Receiving Hormone Replacement Therapy*," European Journal Oral Science, ISSN 0909-883, Munksgaard, 1996; 104: pp. 10-12.

Michael Pharoah, "*X-Ray Film, Intensifying Screens, and Grids,*" (*Excerp from: Oral Radiology: Principles and Interpretation*), 4th Ed., S.C. White, Publisher: Mosby, Inc., pp. 68-76.

\* cited by examiner

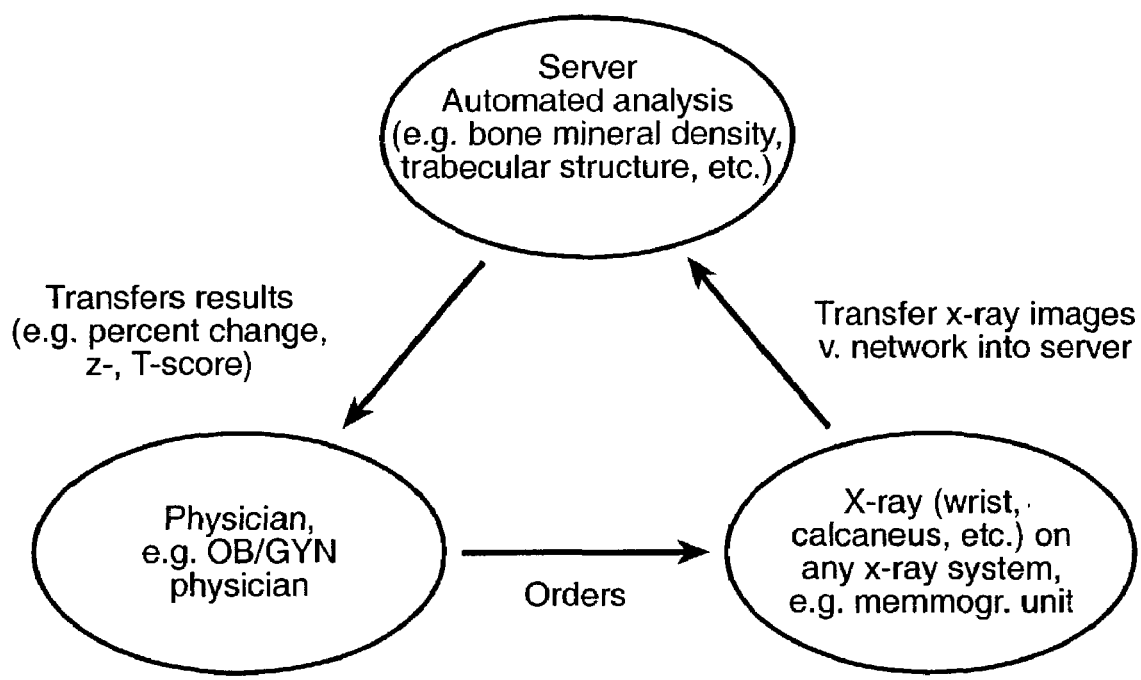
FIG._1

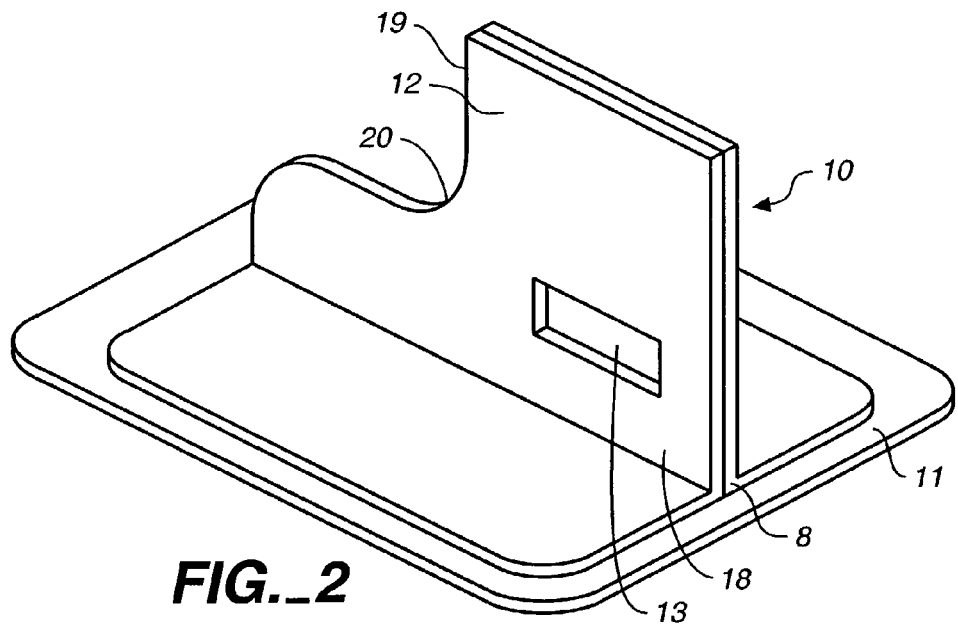
FIG._2
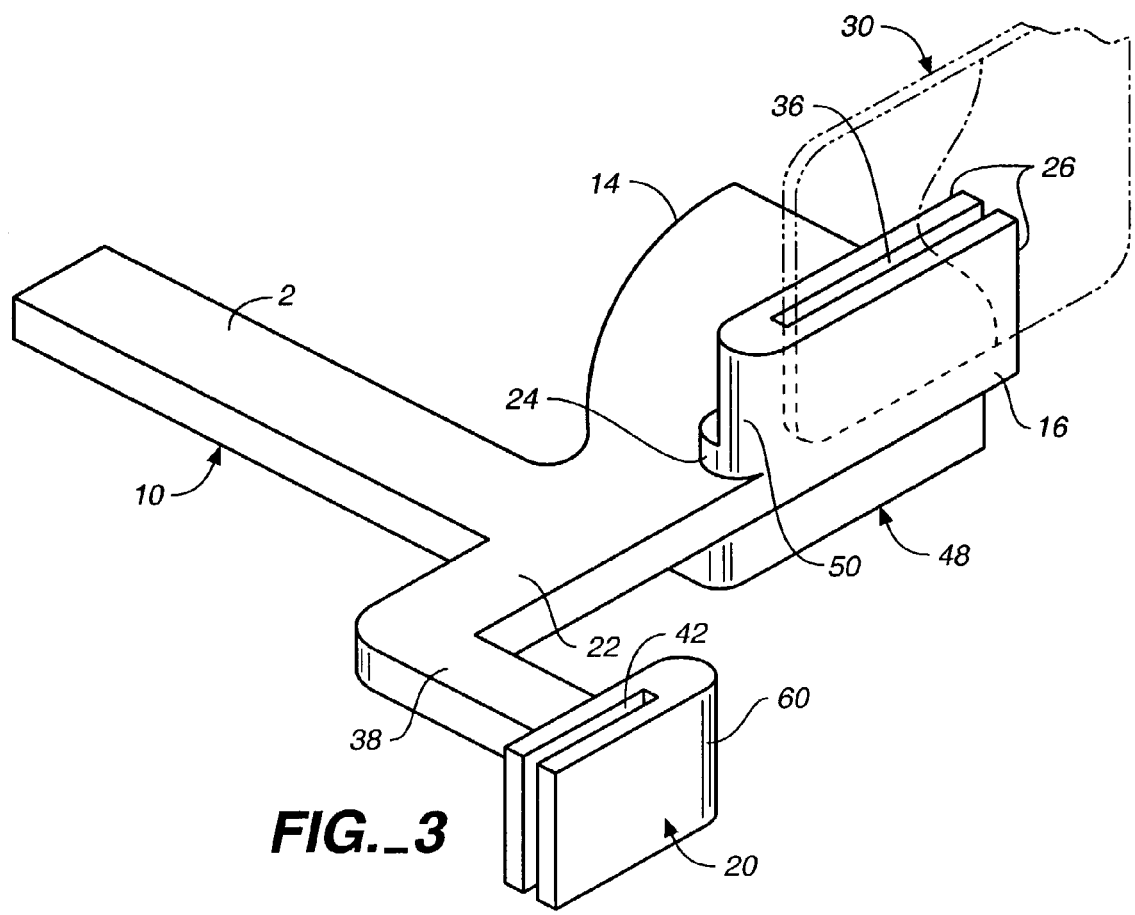
FIG._3

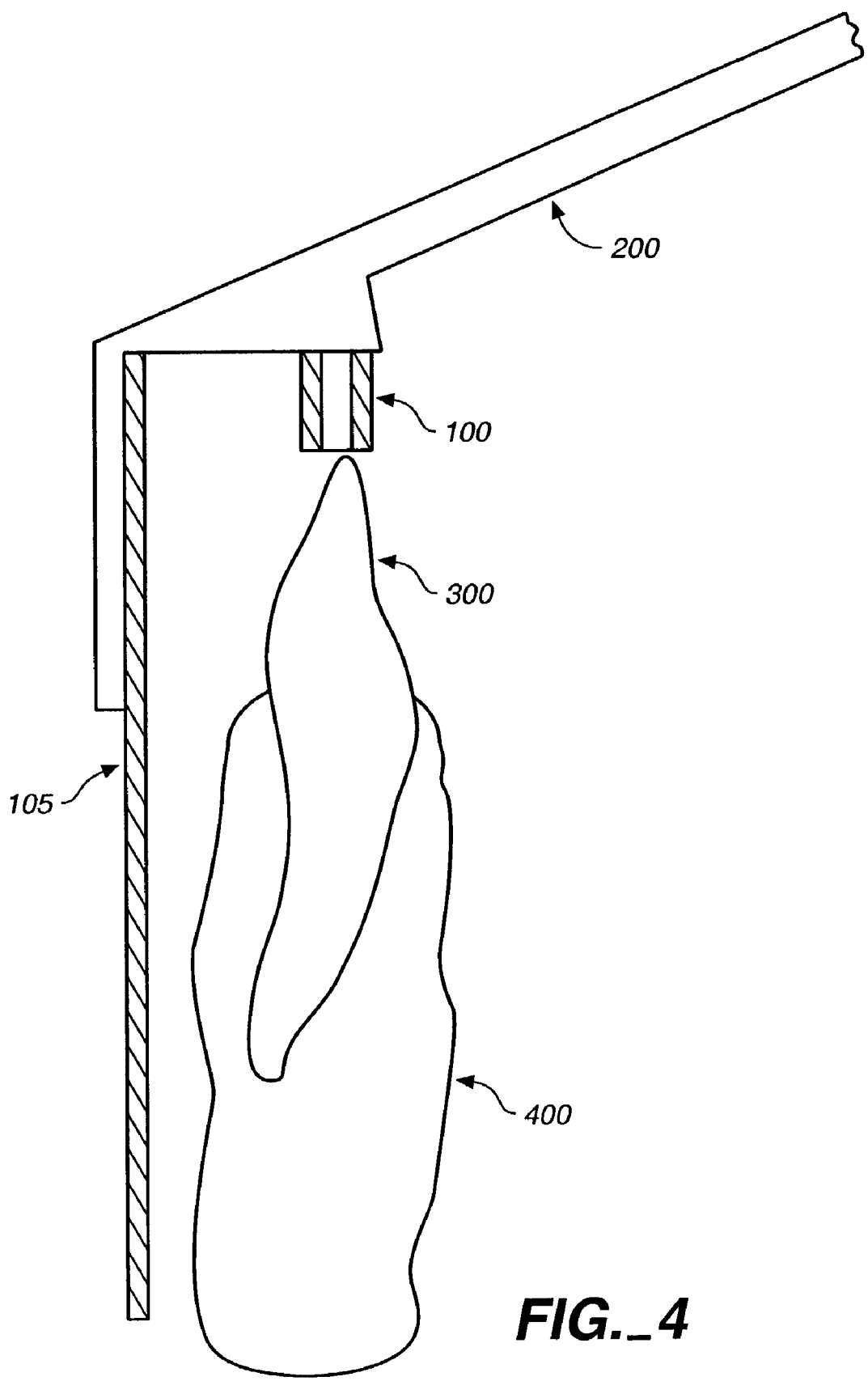
FIG._4

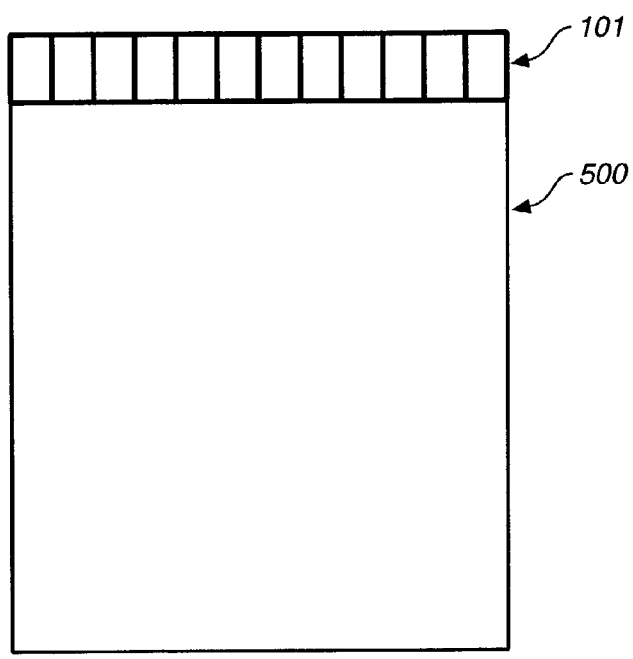
FIG._5
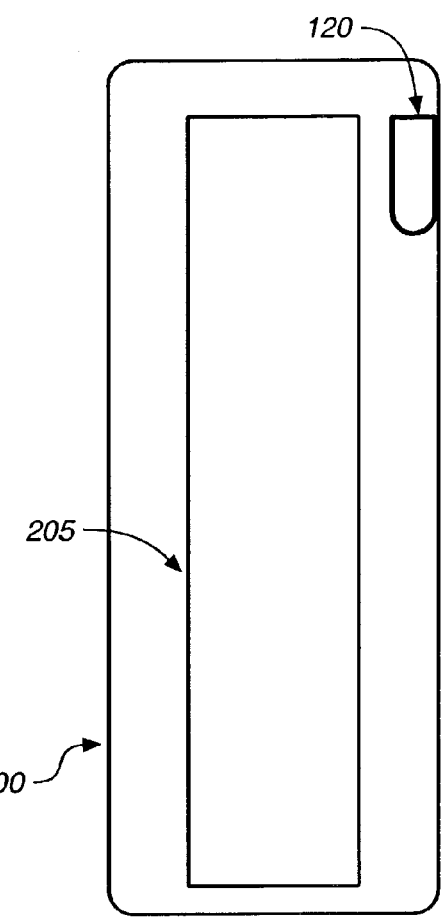
FIG._6
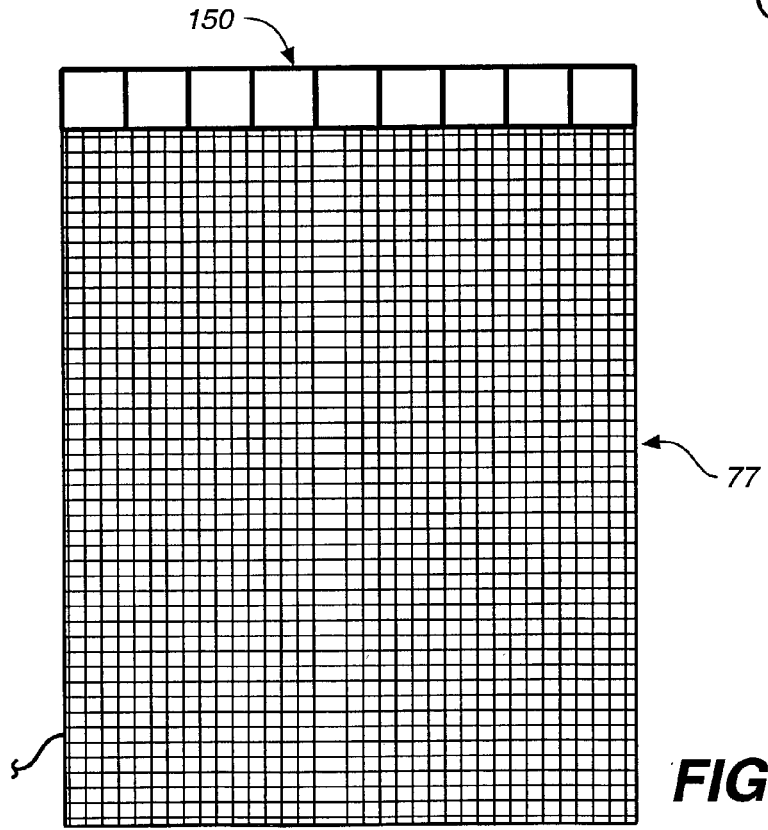
FIG._7

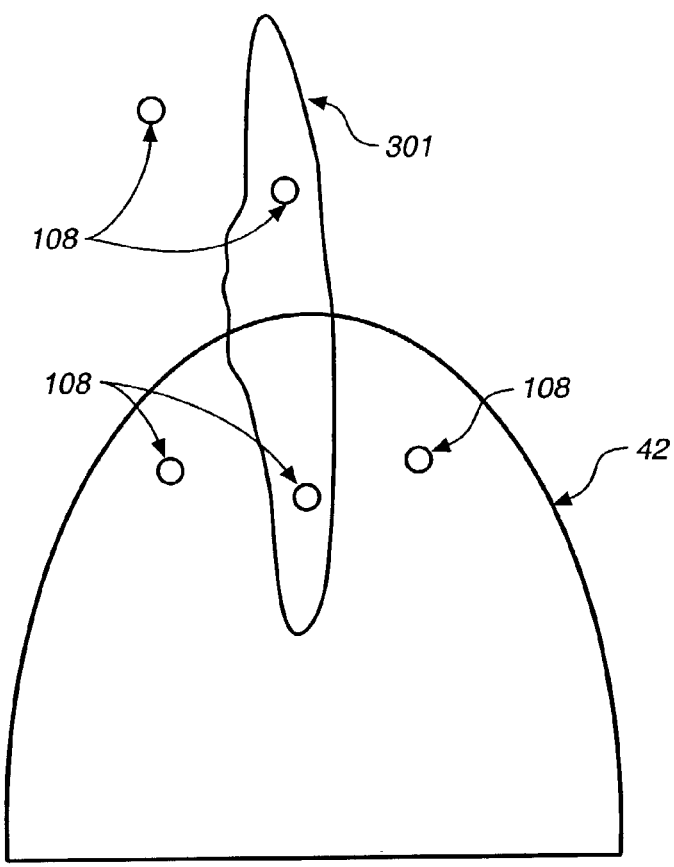
FIG._8
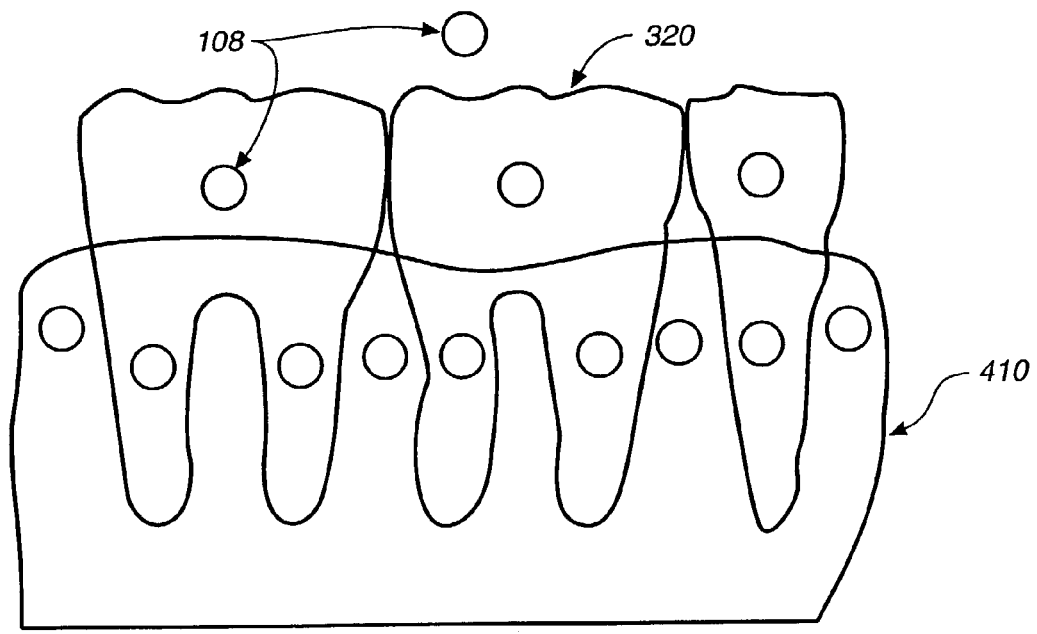
FIG._9

METHODS AND DEVICES FOR QUANTITATIVE ANALYSIS OF X-RAY IMAGES

CROSS-REFERENCE TO RELATED APPLICATIONS

This application is a continuation-in-part of U.S. Ser. No. 10/086,653, filed Feb. 27, 2002, which in turn is a continuation-in-part of U.S. Ser. No. 09/942,528, filed Aug. 29, 2001, which in turn claims the benefit of U.S. Provisional Patent Application Ser. No. 60/228,591, filed Aug. 29, 2000, all of which applications are incorporated herein by reference in their entirety.

TECHNICAL FIELD

The present invention is in the field of radiographic imaging and analysis thereof. In particular, network enabled analyses and analysis techniques are described. Also described are devices comprising calibration phantoms and methods of using these devices.

BACKGROUND

X-rays and other radiographic analysis are important diagnostic tools. Furthermore, it is common practice to transmit x-ray images via local and long-distance networks. Current technology, however, does not allow for the accurate determination of quantitative information contained in the x-ray such as the density of an anatomic structure when x-ray images are transmitted in a network environment.

Calibration references (also known as calibration phantoms) for use in imaging technologies have also described. See, e.g., U.S. Pat. No. 5,493,601 and U.S. Pat. No. 5,235,628. U.S. Pat. No. 5,335,260 discloses a calibration phantom representative of human tissue containing variable concentrations of calcium that serves as reference for quantifying calcium, bone mass and bone mineral density in radiography and CT imaging systems. However, currently-available calibration phantoms are not always accurate, due to both the effect of structures or materials that project on or with the calibration phantom and, additionally, to the fact that one or more regions of the calibration phantom do not always appear on the x-ray image.

Thus, there remains a need for methods for quantitative assessment of information contained in x-ray images such as the density of an anatomic structure in a network environment. There also remains a need for devices and methods that include dependable and accurate calibration phantoms.

SUMMARY

The present invention meets these and other needs by providing compositions and methods that allow for the analysis of x-ray images in a network environment. Also provided are x-ray assemblies comprising accurate calibration phantoms including, in particular, calibration phantoms which act as references in order to determine bone mineral density from an x-ray image.

In one aspect, the invention includes a method for deriving quantitative information from an x-ray image in a network environment comprising, providing a local computer for transmitting the x-ray image, providing a remote computer for receiving the x-ray image and providing a computer program to analyze and extract quantitative information from the x-ray image. In certain embodiments, the quantitative information is densitometric information, for example bone mineral density or density of selected soft-tissues or organs. Alternatively, the quantitative information is information on the morphology of a structure, for example information on the two-dimensional arrangement of individual components forming said structure or information on the three-dimensional arrangement of individual components forming said structure. In any of the methods described herein, the structure can be bone and the information can be, for example, information on trabecular thickness, trabecular spacing and/or estimates of the two- or three-dimensional architecture of the trabecular network. Further, in any of the methods described herein, quantitative information can be derived with use of an external standard, for example a calibration phantom of known x-ray density. (e.g., a calibration phantom is included with the structure to be imaged on the x-ray image).

In other embodiments, the quantitative information derived from the x-ray image includes one or more parameters relating to the acquisition of the x-ray image (e.g., x-ray tube voltage, x-ray energy, x-ray tube current, film-focus distance, object-film distance, collimation, focal spot size, spatial resolution of the x-ray system, filter technique, film focus distance, correction factor(s) or combinations thereof), for instance to improve the accuracy of the quantitative information. The x-ray acquisition parameters can be transferred over the network prior to, simultaneously or after transmission of the x-ray image. Furthermore, one or more of the x-ray acquisition parameters can be entered either manually or, alternatively, automatically into a computer.

In another aspect, a method for measuring quantitative information in an x-ray image in a network environment is provided. In certain embodiments, the method comprises transmitting an x-ray image from a local computer to a remote computer and obtaining quantitative information from the x-ray image using a computer program. In certain embodiments, one or more internal standard is provided in (or with) the x-ray image or the computer program. The internal standard can be, for example, density of a tissue of a human (e.g., subcutaneous fat, bone, muscle), air surrounding a structure or combinations of tissue and air density. In other embodiments, one or more external standards are provided in (or with) the x-ray image or computer program. The at least one external standard (e.g., calibration phantom can be temporarily or permanently physically connected to the x-ray film with use of an attachment mechanism, for example a mechanical attachment mechanism such as Velcro or adhesive. Additionally, the at least one external standard can be integrated into the film and/or film holder, for example by including a material of known x-ray density between two of the physical layers of the x-ray film or by including a material of know x-ray density within one of the physical layers of the x-ray film.

In other aspects, any of the methods described herein further comprise the steps of generating a diagnostic report based on the quantitative information and, optionally, sending the diagnostic report (for example to a physician). Such reports can be generated using computer programs, for example programs on the remote computer. The diagnostic report can include, for example, information on a patient's state of health (e.g., bone mineral density status such as osteoporosis and/or information on fracture risk). Other disease states can also be analyzed from x-ray images using the teachings described herein. In certain embodiments, these methods further comprise generating a bill (accounting of charges) for the recipient of the diagnostic report. The bill can include charges for generating the report, profession fees, technical fees or the like. The bill can be printed and transmitted by mail or by fax to the recipient or the bill can be electronically transmitted. The recipient can be a physician, a subject, a patient, the patient's employer, a health maintenance organization, health insurance provider, a government agency, or government representative. The bill can also be divided and various portions thereof sent to multiple recipients. In certain embodiments, the bill is generated using a computer program on the remote computer.

In another aspect, the invention includes a method of formulating one or more x-ray image data databases, said method comprising collecting x-ray image data (e.g., densiometric information) from one or more subjects, formulating said one or more data databases by associating each of said data points with one or more data attributes (e.g., age of subject, weight of subject, height of subject, disease state, etc. The data can be collected using x-ray imaging techniques, for example by using digital or digitized x-ray images. In certain embodiments, the data is from a single subject while in other embodiments, the data is from two or more subjects. In other embodiments, the methods further comprise compiling multiple databases from each database where the data points are collected from a single individual and the data points for each single individual are associated with one or more relevant data attributes.

In any of the methods described herein, the quantitative information can be densitometric information, for example bone mineral density or density of selected soft-tissues or organs. Alternatively, the quantitative information is information on the morphology of a structure, for example information on the two-dimensional arrangement of individual components forming said structure or information on the three-dimensional arrangement of individual components forming said structure. In any of the methods described herein, the structure can be bone and the information can be, for example, information on trabecular thickness, trabecular spacing and/or estimates of the two- or three-dimensional architecture of the trabecular network. Furthermore, the information can be encrypted in any of the methods described herein (e.g., to hide the subject's name or other demographic information from unauthorized users).

Furthermore, in any of the methods described herein, the x-ray image can be derived from x-ray film, for example using a phosphorous plate system. Preferably, the image is digitized, for example, the image may be acquired digitally (e.g., using a selenium or silicon detector system) or digitized using a scanning unit.

In another aspect, the invention includes databases made by any of the methods described herein, for example by formulating data points collected from x-ray images. In certain embodiments, the data points are associated with one or more relevant data attributes.

In another aspect, a method of manipulating an x-ray image data database, comprising providing any of the databases comprising data points and data attributes described herein; and manipulating said data points via said attributes associated with said data points to determine relationships between said data points and said attributes.

In another aspect, the invention includes an x-ray assembly for determining bone mineral density comprising an x-ray film holder; x-ray film and a calibration phantom comprising at least one marker, for example, a line, or other geometric pattern (e.g., circles, stars, squares, crescents, ovals, multiple-sided objects, irregularly shaped objects or combinations of any of these shapes) positioned in an area of known density and wherein the calibration phantom projects free of bone tissue. The calibration phantom can be attached to the x-ray film, the film holder and/or the detection system. The attachment can be permanent (e.g., integral to the film such as between two physical layers of the film or within one layer of the film, and/or integral to the film holder or detector) or temporary (e.g., via a mechanical or other attachment mechanism such as Velcro, adhesive or the like). Thus, in certain embodiments, the calibration phantom is reusable and/or can be sterilized between uses. In certain embodiments, the assembly is a dental x-ray assembly. In any of the x-ray assemblies described herein, the calibration phantom can be shaped, for example, as a stepwedge or as a plurality of fluid-filled chambers of known densities.

In certain aspects, a wedge-shaped calibration phantom is used to provide reference measurements to express the density of an anatomic structure in terms of thickness of the phantom material. For example, described herein are methods of generating a calibration curve describing the relationship between measured attenuation and material thickness wherein the data points making up the curve are derived from the image of the phantom. In certain embodiments, the wedge-shaped calibration phantom has a length L and a linear change from a maximum thickness T to thickness 0 over the length (e.g., the calibration phantom has two ends—one marking the thinnest point and one the thickest, where thickness varies linearly between the two ends). In these embodiments, each point X in the image of the wedge at distance D from the thin end of the wedge results in a point (T*L/D, G) of the calibration curve, where T*L/D is the thickness of the wedge at X and G the attenuation at X.

Alternatively, calibration curves can also be generated when the distance D is unknown, for example if the calibration wedge varies non-linearly over its length or both ends of the phantom cannot be properly identified in the image. In certain embodiments, the shape of the expected entire calibration curve is determined, and the part of the curve that can be calculated from the identified regions of the calibration wedge is fitted to the expected curve. For a known attenuation of a particular anatomic structure, the corresponding thickness value is determined with use of said calibration curve.

Furthermore, calibration curves generated from both linear and non-linear phantoms can be further manipulated, for example to translate thickness data into concentration (e.g., calcium concentration). In certain embodiments, the image of an aluminum step wedge and a calibration curve expressing thickness is translated into units of calcium concentration by including samples of varying calcium concentration in the image. Using this second calibration curve, values expressed in aluminum thickness can be converted into units of calcium concentration.

In still further embodiments, a reference calibration curve can be generated, for example by averaging a plurality of calibration curves obtained by any of the methods described herein (e.g., thickness and/or concentration curves). Reference calibration curves find use in analysis of images that do not have their own phantoms or other standards.

In yet another aspect, the invention includes methods of obtaining accurate bone mineral density information using any of the calibration phantoms and/or methods described herein. Thus, in certain embodiments, the methods comprise positioning any of the calibration phantoms described herein such that x-rays pass through a subject and the calibration phantom simultaneously, wherein the calibration phantom projects free of materials that alter its' apparent density; creating an image of the phantom and the portion of the subject's anatomy; and comparing the image of the phantom and the subject's anatomy to determine bone mineral density of the subject. The x-ray image can be, for example, a dental x-ray. Any of the methods described herein can be performed on a computer, in a network environment, or manually.

Another aspect of the invention is a kit for aiding in assessing the condition of bone in a subject, which kit comprises a software program, which that when installed and executed on a computer reads an x-ray image (e.g. a digital or digitized dental x-ray) and produces a computer readout showing bone mineral density. Any of the kits described herein can also include a calibration phantom, x-ray film, x-ray film holders and computer programs (e.g., software) for displaying and/or generating a bill for the readout regarding bone mineral density.

In other aspects, the invention includes a calibration phantom, for example a calibration phantom comprising a plurality of geometric shapes, wherein the calibration phantom is less than 2.5 cm in length and less than 5 mm in width. The geometric shapes may be for example, comprise rectangles that form a step-wedge. The phantom itself may be stainless steel for example 0.08% carbon, 2% manganese, 1% silicon, 0.045% phosphorus, 0.03% sulphur; 10–14% nickel, 16–18% chromium, 2–3% molybdenum and iron up to 100%.

In yet another aspect, methods of diagnosing osteoporosis in a subject are provided, for example using any of the kits, methods and/or devices described herein. In certain embodiments, the methods of diagnosing osteoporosis in a subject comprise using a computer program to analyze bone mineral density of an x-ray image and comparing the bone mineral density value obtained from the image with a reference standard or curve, thereby determining if the subject has osteoporosis. In certain embodiments, the x-ray image includes a calibration phantom, for example a calibration phantom as described herein. In other embodiments, a reference calibration curve can be used to analyze the image.

In still further aspects, methods of assessing bone mineral density are used to provide suitable treatment for a subject in need thereof. For instance, using any of the methods, kits, and/or devices described herein, the presence of osteoporosis in a subject can be diagnosed and that subject provided with appropriate therapy (e.g., one or more anti-resorptive agents and/or one or more anabolic agents). Additionally, over time, the methods described herein can be used to assess the efficacy of the selected treatment. Thus, in certain embodiments, diagnosis and/or treatment of osteoporosis are achieved in a network-enabled environment.

These and other embodiments of the subject invention will readily occur to those of skill in the art in light of the disclosure herein.

BRIEF DESCRIPTION OF THE FIGURES

FIG. 1 depicts an example of network enabled quantitative x-ray analysis useful in monitoring osteoporosis.

FIG. 2 depicts an exemplary dental x-ray film holder. The film holder includes a calibration phantom.

FIG. 3 depicts another exemplary dental x-ray film holder. The film holder includes a calibration phantom.

FIG. 4 depicts an exemplary embodiment in which a calibration phantom is attached to a dental x-ray film holder.

FIG. 5 depicts an exemplary embodiment in which a calibration phantom is attached to x-ray film.

FIG. 6 depicts an exemplary embodiment in which a calibration phantom is integrated into a film cover.

FIG. 7 depicts an exemplary embodiment in which a calibration phantom is integrated into a detector system.

FIG. 8 depicts exemplary measurement sites in a dental x-ray that can be used as an intrinsic standard to calibrate the image.

FIG. 9 depicts exemplary measurement sites in a dental x-ray that can be used as an intrinsic standard to calibrate the image.

FIG. 12, panel A, is a front view of an exemplary calibration phantom comprising a plurality of rectangles that form a stepwedge shape. FIG. 12, panel A, also depicts optional geometric shapes or patterns that can be positioned at points of known density in the calibration phantom. FIG. 12, panel B, is an overview of an exemplary calibration phantom in which the thickness of the calibration phantom varies linearly along the length. FIG. 12, panel C, is an overview of an exemplary calibration phantom in which the thickness of the calibration phantom varies non-linearly along the length.

DETAILED DESCRIPTION

Figure 10:
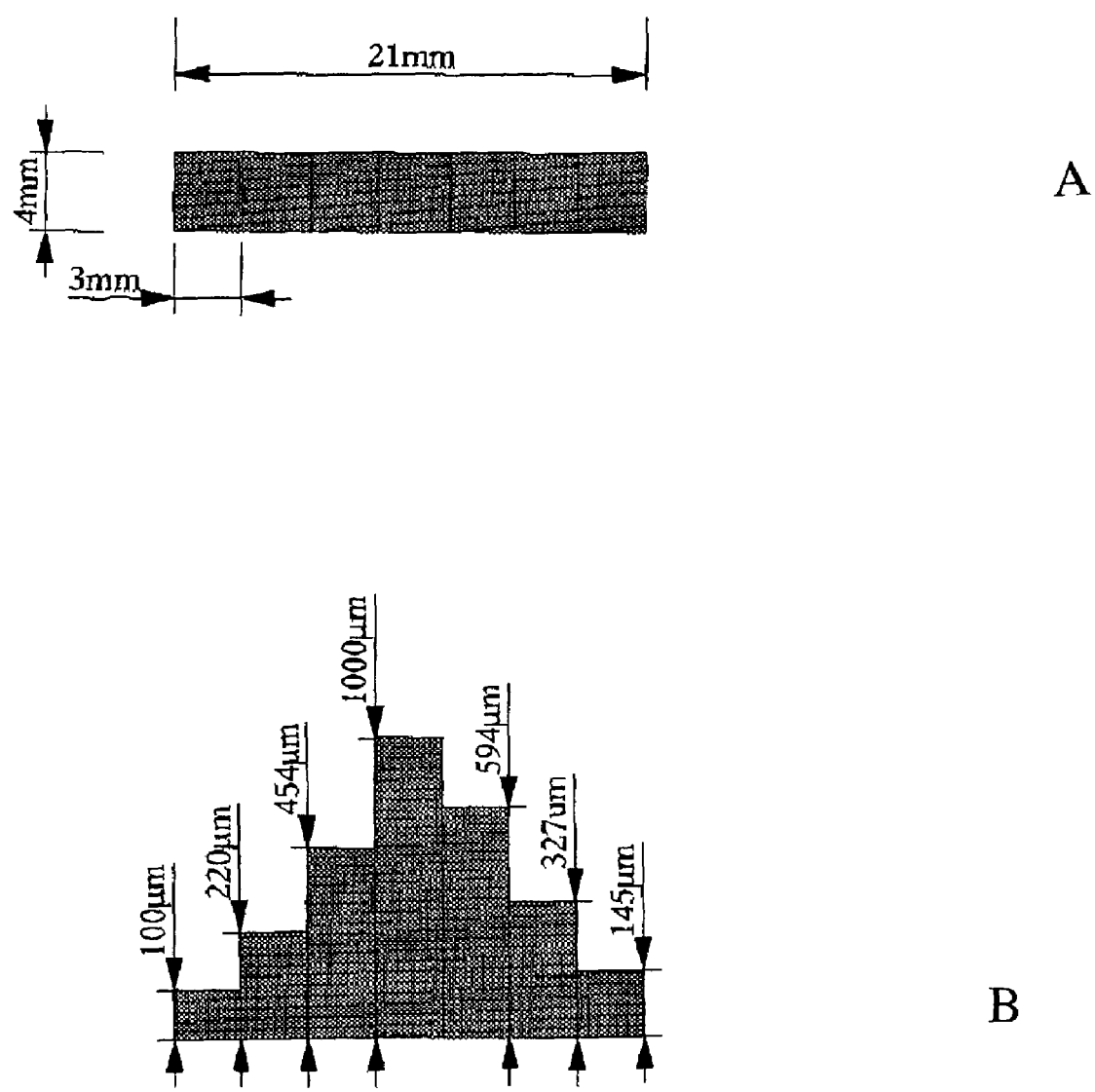
FIG. 10, panels A and B, depict an exemplary calibration phantom. Panel (A) shows a top view and the dimensions of the device. Panel (B) shows the side view of the step-wedge and exemplary dimensions.
Figure 11:
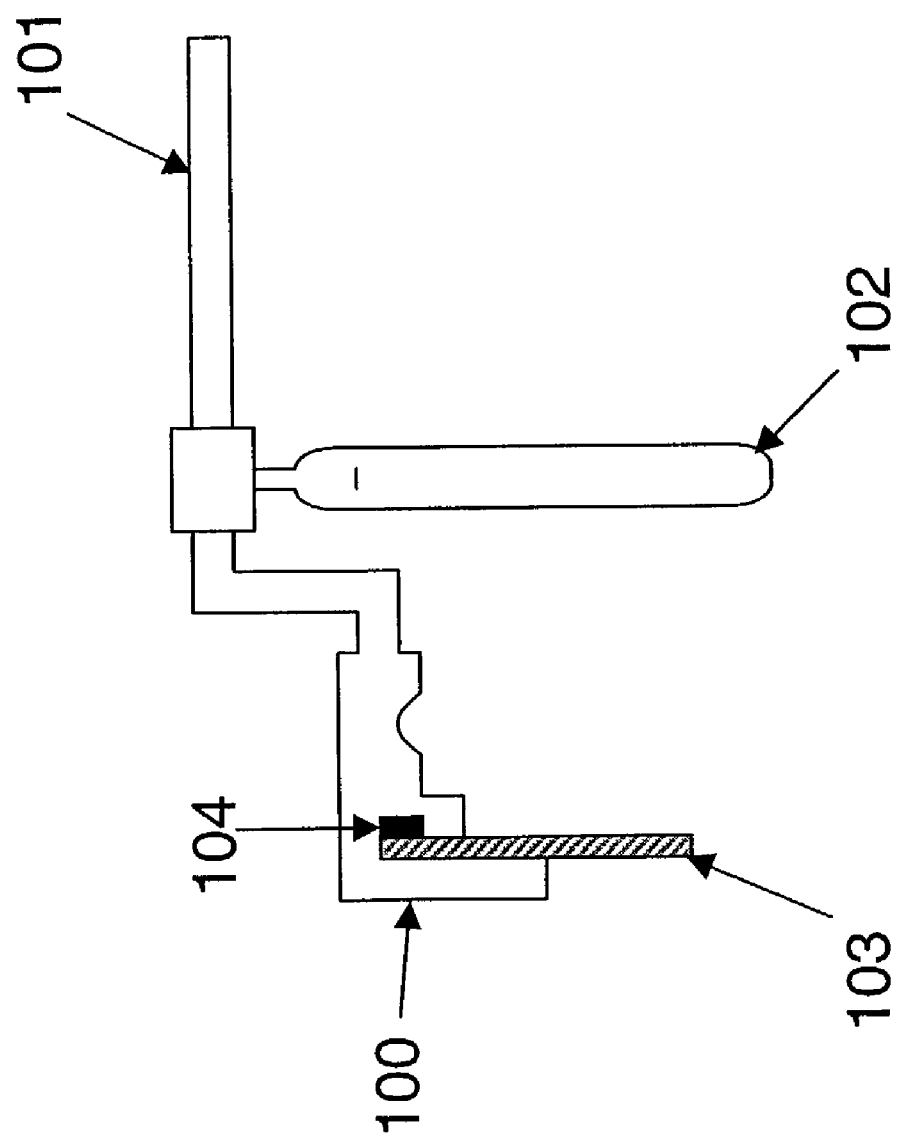
FIG. 11 depicts a side-view of an exemplary x-ray system for dental x-rays in which a calibration phantom (104) is integrated into the film holder. Also shown in FIG. 11 are bite block (100), film (103), ring-shaped Rinn holder (102) and stainless steel rod (101). The ring-shaped Rinn holder can help align the x-ray tube so that it is perpendicular or near perpendicular to the film.
Figure 12A:
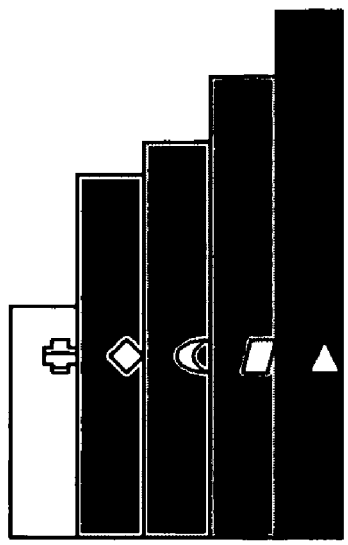
FIG. 12, panels A to C, depict exemplary wedge-shaped calibration phantoms as described herein.
Figure 12B:
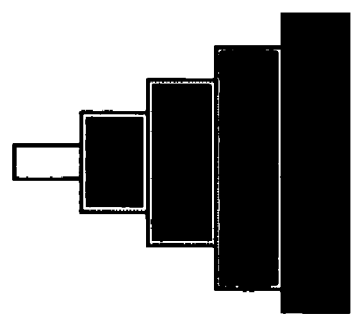
Figure 12C:
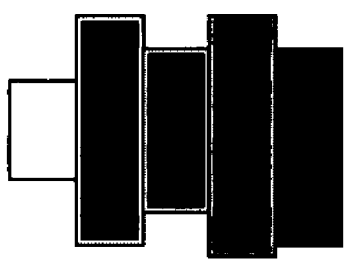

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

The practice of the present invention employs, unless otherwise indicated, conventional methods of database storage and manipulation, within the skill of the art. Such techniques are explained fully in the literature. See, e.g., Numerical Mathematical Analysis, Third Edition, by J. B. Scarborough, 1955, John Hopkins Press, publisher; System Analysis and Design Methods, by Jeffrey L. Whitten, et al., Fourth Edition, 1997, Richard D. Irwin, publisher; Modern Database Management, by Fred R. McFadden, et al., Fifth Edition, 1999, Addison-Wesley Pub. Co., publisher; Modern System Analysis and Design, by Jeffery A. Hoffer, et al., Second Edition, 1998, Addison-Wesley Pub. Co., publisher; Data Processing: Fundamentals, Design, and Implementation, by David M. Kroenke, Seventh Edition, 2000, Prentice Hall, publisher; Case Method: Entity Relationship Modelling (Computer Aided Systems Engineering), by Richard Barker, 1990, Addison-Wesley Pub Co., publisher.

All publications, patents and patent applications cited herein, whether above or below, are hereby incorporated by reference in their entirety.

It must be noted that, as used in this specification and the appended claims, the singular forms "a", "an", and "the" include plural referents unless the content clearly dictates otherwise. Thus, for example, reference to "a calibration phantom" includes a one or more such phantoms.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and, thus, includes adult and newborn subjects, whether male or female.

"Parameter" refers to an arbitrary constant or variable so appearing in a mathematical expression that changing it gives various cases of the phenomenon represented (McGraw-Hill Dictionary of Scientific and Technical Terms, S. P. Parker, ed., Fifth Edition, McGraw-Hill Inc., 1994). A parameter is any of a set of properties whose values determine the characteristics or behavior of something.

A "data point", generally, is a numeric value which corresponds to a physical measurement (an "acquired" datum or data point) or to a single numeric result calculated or derived from one or more acquired data points (a "calculated" or "derived" datum or data point). Derived data include, but are not limited to, derived quantities from original data, such as, rate and/or magnitude of change, slope of a line (e.g., as determined by regression analysis), an intercept (e.g., as determined by regression analysis), and correlation coefficients.

"Data tags," also referred to as "attributes" of a data point, are various characteristics of the particular data point with which they are associated. For example, data points comprising x-ray information (and/or bone mineral density) are associated with a number of attributes, e.g., the date and time the image was taken; certain identification related to the particular subject from which the measurement was made (e.g., demographic information such as the particular user's sex, age, weight or race; medical information e.g., the medications used by the subject and/or type of disease suffered by the subject).

A "database" is a collection of data points and data attributes associated with each data point. Thus, a "data points, derived data, and data attributes database" is a database comprising data points collected, e.g. from an x-ray image, data derived from the original data points and the data attributes associated with those data points or the derived data. A database may be limited to data points comprising measurements of one or more levels; those data points may further be collected from one or more subjects. For example, one data point database may be created and the information in the database related to a second database of attributes. Such combinations of one or more databases are within the skill of one of ordinary skill in the art in view of the teachings of the present specification. A "data warehouse" is another term for database. The term data warehouse is typically applied to large databases.

"Formulation" of a database comprises collecting data points, inputting those data points into a desired database format, and associating various attributes with each data point according to the particular format employed. A wide variety of software exists which provides a means for inputting data points, and associating the data points with data attributes, such as Excel® (Microsoft® Corporation, Seattle, Wash.) spreadsheet software, Quattro® (Corel Inc., Ottawa, Canada) spreadsheet software, Microsoft Access 2000® (Microsoft) software, Oracle® (Oracle Inc., Redwood Shores, Calif.) software, as well as other database and data warehousing software.

"Manipulation" of a database refers to a variety of processes, e.g., selecting, sorting, sifting, aggregating, clustering, modeling, exploring, and segmenting data points using various data attributes or tags associated with the data points. Available systems for generating databases and manipulating the resulting databases include but are not limited to Sybase® (Sybase Systems, Emeryville, Calif.), Oracle® (Oracle Inc., Redwood Shores, Calif.), and Sagent Design Studio® (Sagent Technologies Inc., Mountain View, Calif.) systems software. Further, statistical packages and systems for data analysis and data mining are also available. Illustrative examples include SAS® (SAS Institute Inc., Cary, N.C.) and SPSS® (SPSS Inc., Chicago, Ill.) systems software.

"Data mining" refers to the process of selecting, exploiting, modeling, etc., large amounts of data to uncover previously unknown trends, patterns, and relationships within and among various data points and data attributes.

"Data aggregation" and "data clustering" refers to the process of grouping data points on the basis of one or more common attributes. Conversely, "data segmentation" refers to the process of differentiating data into discrete groups on the basis of one or more attributes.

General Overview

Methods and compositions useful in analyzing x-ray images are described. In particular, the invention includes methods of obtaining and/or deriving information from an x-ray image in network environment. Additionally, the present invention relates to the provision of accurate calibration phantoms for X-ray systems and methods of using these calibration phantoms. Typically, the calibration phantom is formed of a material that simulates the properties of human bone tissue and is provided in an x-ray assembly such that improved accuracy and precision in the quantification of calcium, bone mass and bone density using conventional X-ray equipment is achieved.

Advantages of the present invention include, but are not limited to, (i) providing fast, centralized networks for the analysis of x-ray images, particularly analysis of x-rays for bone mineral density; (ii) providing accessible and reliable means for analyzing x-rays; (iii) providing accurate calibration phantoms; (iv) providing accurate calibration phantoms that can be readily used with standard x-ray technology; and (v) providing methods and materials for making these network-enabled techniques and devices.

Database Formulation

The method of formulating data points, derived data, and data attributes database according to the present invention may comprise the following: (1) the collection of data points, said data points comprising information obtained from an x-ray image, for example, bone mineral density information; and (2) the association of those data points with relevant data point attributes. The method may further comprise (3) determining derived data points from one or more direct data points and (4) associating those data points with relevant data point attributes. The method may also comprise (5) collection of data points using a remote computer whereby said remote computer operates in a network environment.

In preferred embodiments, the information is obtained from an x-ray image, for example of an anatomical structure or of a non-living structure. X-ray images can be acquired at a local site using known techniques. If the x-ray image was captured using conventional x-ray film, the data points (information) of the x-ray image can be digitized using a scanning device. The digitized x-ray image information can then be transmitted over the network, e.g. the Internet, into a remote computer or server. If the x-ray image was acquired using digital acquisition techniques, e.g. using phosphorus plate systems or selenium or silicon detector systems, the x-ray image information is already available in digital format. In this case the image can be transmitted directly over the network, e.g. the Internet. The information can also be compressed and/or encrypted prior to transmission. Transmission can also be by other methods such as fax, mail or the like.

Data Points

Thus, the methods of formulating data points, derived data, and data attributes database that forms an aspect of the present invention begins with the collection of data sets of measurement values, for example measurements of bone mineral density from x-ray images. Records may be formulated in spreadsheet-like format, for example including data attributes such as date of x-ray, patient age, sex, weight, current medications, geographic location, etc. The database formulation method of the present invention may further comprise the calculation of derived or calculated data points from one or more acquired data points. A variety of derived data points may be useful in providing information about individuals or groups during subsequent database manipulation, and are therefore typically included during database formulation. Derived data points include, but are not limited to the following: (1) maximum bone mineral density, determined for a selected region of bone or in multiple samples from the same or different subjects; (2) minimum bone mineral density, determined for a selected region of bone or in multiple samples from the same or different subjects; (3) mean bone mineral density, determined for a selected region of bone or in multiple samples from the same or different subjects; (4) the number of measurements that are abnormally high or low, determined by comparing a given measurement data point with a selected value; and the like. Other derived data points will be apparent to persons of ordinary skill in the art in light of the teachings of the present specification. The amount of available data and data derived from (or arrived at through analysis of) the original data provide provides an unprecedented amount of information that is very relevant to management of bone related diseases such as osteoporosis. For example, by examining subjects over time, the efficacy of medications can be assessed.

Measurements and derived data points are collected and calculated, respectively, and may be associated with one or more data attributes to form a database.

Data attributes can be automatically input with the x-ray image and can include, for example, chronological information (e.g., DATE and TIME). Other such attributes may include, but are not limited to, the type of x-ray imager used, scanning information, digitizing information and the like. Alternatively, data attributes can be input by the subject and/or operator, for example subject identifiers, i.e. characteristics associated with a particular subject. These identifiers include but are not limited to the following: (1) a subject code (e.g., a numeric or alpha-numeric sequence); (2) demographic information such as race, gender and age; (3) physical characteristics such as weight, height and body mass index (BMI); (4) selected aspects of the subject's medical history (e.g., disease states or conditions, etc.); and (5) disease-associated characteristics such as the type of bone disorder, if any; the type of medication used by the subject. In the practice of the present invention, each data point would typically be identified with the particular subject, as well as the demographic, etc. characteristic of that subject.

Other data attributes will be apparent to persons of ordinary skill in the art in light of the teachings of the present specification.

Storage of Data Sets and Association of Data Points with Relevant Data Attributes A number of formats exist for storing data sets and simultaneously associating related attributes, including but not limited to (1) tabular, (2) relational, and (3) dimensional. In general the databases comprise data points, a numeric value which correspond to physical measurement (an "acquired" datum or data point) or to a single numeric result calculated or derived from one or more acquired data points that are obtained using the various methods disclosed herein. The databases can include raw data or can also include additional related information, for example data tags also referred to as "attributes" of a data point. The databases can take a number of different forms or be structured in a variety of ways.

The most familiar format is tabular, commonly referred to as a spreadsheet. A variety of spreadsheet programs are currently in existence, and are typically employed in the practice of the present invention, including but not limited to Microsoft Excel spreadsheet software and Corel Quattro spreadsheet software. In this format, association of data points with related attributes occurs by entering a data point and attributes related to that data point in a unique row at the time the measurement occurs.

Further, rational, relational (Database Design for Mere Mortals, by Michael J. Hernandez, 1997, Addison-Wesley Pub. Co., publisher; Database Design for Smarties, by Robert J. Muller, 1999, Morgan Kaufmann Publishers, publisher; Relational Database Design Clearly Explained, by Jan L. Harrington, 1998, Morgan Kaufmann Publishers, publisher) and dimensional (Data-Parallel Computing, by V. B. Muchnick, et al., 1996, International Thomson Publishing, publisher; Understanding Fourth Dimensions, by David Graves, 1993, Computerized Pricing Systems, publisher) database systems and management may be employed as well.

Relational databases typically support a set of operations defined by relational algebra. Such databases typically include tables composed of columns and rows for the data included in the database. Each table of the database has a primary key, which can be any column or set of columns, the values for which uniquely identify the rows in a table. The tables in the database can also include a foreign key that is a column or set of columns, the values of which match the primary key values of another table. Typically, relational databases also support a set of operations (e.g., select, join and combine) that form the basis of the relational algebra governing relations within the database.

Such relational databases can be implemented in various ways. For instance, in Sybase® (Sybase Systems, Emeryville, Calif.) databases, the tables can be physically segregated into different databases. With Oracle® (Oracle Inc., Redwood Shores, Calif.) databases, in contrast, the various tables are not physically separated, because there is one instance of work space with different ownership specified for different tables. In some configurations, databases are all located in a single database (e.g., a data warehouse) on a single computer. In other instances, various databases are split between different computers.

It should be understood, of course, that the databases are not limited to the foregoing arrangements or structures. A variety of other arrangements will be apparent to those of skill in the art.

Database Manipulation

Databases formulated using the methods of the present invention are useful in that they can be manipulated, for example, using a variety of statistical analyses, to produce useful information. The databases of the present invention may be generated, for example, from data collected for an individual or from a selected group of individuals over a defined period of time (e.g., days, months or years), from derived data, and from data attributes.

The present invention further relates to a method for manipulating data points, derived data, and data attributes database in order to provide a useful result, said method comprising providing data points, derived data, and data attributes database, and manipulating and/or analyzing the database.

For example, data sets may be aggregated, sorted, selected, sifted, clustered and segregated by means of the attributes associated with the data points. A number of database management systems and data mining software programs exist which may be used to perform the desired manipulations.

Relationships in the database can be directly queried and/or the data analyzed by statistical methods to evaluate the information obtained from manipulating the database.

For example, a distribution curve can be established for a selected data set, and the mean, median and mode calculated therefor. Further, data spread characteristics, e.g. variability, quartiles and standard deviations can be calculated.

The nature of the relationship between a particular variable and bone mineral density levels can be examined by calculating correlation coefficients. Useful methods for doing so include but are not limited to the following: Pearson Product Moment Correlation and Spearman Rank Order Correlation.

Analysis of variance permits testing of differences among sample groups to determine whether a selected variable has a discernible effect on the parameter being measured.

Non-parametric tests may be used as a means of testing whether variations between empirical data and experimental expectancies are attributable merely to chance or to the variable or variables being examined. These include the Chi Square test, the Chi Square Goodness of Fit, the 2×2 Contingency Table, the Sign Test, and the Phi Correlation Coefficient.

There are numerous tools and analyses available in standard data mining software that can be applied to the analysis of the databases of the present invention. Such tools and analyses include, but are not limited to, cluster analysis, factor analysis, decision trees, neural networks, rule induction, data driven modeling, and data visualization. Some of the more complex methods of data mining techniques are used to discover relationships that are more empirical and data-driven, as opposed to theory-driven, relationships.

Exemplary data mining software that can be used in analysis and/or generation of the databases of the present invention includes, but is not limited to: Link Analysis (e.g., Associations analysis, Sequential Patterns, Sequential time patterns and Bayes Networks); Classification (e.g., Neural Networks Classification, Bayesian Classification, k-nearest neighbors classification, linear discriminant analysis, Memory based Reasoning, and Classification by Associations); Clustering (e.g., k-Means Clustering, demographic clustering, relational analysis, and Neural Networks Clustering); Statistical methods (e.g., Means, Std dev, Frequencies, Linear Regression, non-linear regression, t-tests, F-test, Chi2 tests, Principal Component Analysis, and Factor Analysis); Prediction (e.g., Neural Networks Prediction Models, Radial Based Functions predictions, Fuzzy logic predictions, Times Series Analysis, and Memory based Reasoning); Operating Systems; and Others (e.g., Parallel Scalability, Simple Query Language functions, and C++ objects generated for applications). Companies that provide such software include, for example, the following: Adaptative Methods Group at UTS (UTS City Campus, Sydney, NSW 2000), CSI®, Inc., (Computer Science Innovations, Inc. Melbourne, Fla.), IBM® (International Business Machines Corporation, Armonk, N.Y.), Oracle® (Oracle Inc., Redwood Shores, Calif.) and SAS® (SAS Institute Inc., Cary, N.C.).

These methods and processes may be applied to the databases of the present invention, for example, databases comprising, x-ray image data sets, derived data, and data attributes.

For a general discussion of statistical methods applied to data analysis, see Applied Statistics for Science and Industry, by A. Romano, 1977, Allyn and Bacon, publisher.

Hardware/Software and System Considerations

A. Hardware/Software

Various computer systems, typically comprising one or more microprocessors, can be used to store, retrieve, and analyze information obtained according to the methods described herein. The computer system can be as simple as a stand-alone computer that is not networked to other computers, provided the system has a form of data storage, for example disk drives, removable disk storage, for example ZIP® drives (Iomega Corporation, Roy, Utah), optical medium (e.g., CD-ROM), magnetic tape, solid-state memory, and/or bubble memory. Alternatively, the computer system can include a networked computer system in which a computer is linked to one or more additional computers, for example a network server. The networked system can be an intranet system and/or a system linked to other computers via the Internet. Thus, the computer systems can be Internet-based systems or non-Internet based systems.

In addition, devices such as the Personal Digital Assistants (PDA), for example Palm Pilot™ (Palm Inc., Santa Clara, Calif.) or Handspring™ Visor™ (Handspring, Inc., Mountain View, Calif.) and Pocket PCs (PPC), for example Casio® EM500 Multimedia Cassiopeia Pocket PC (Casio Inc., Dover, N.J.) or Compaq® iPAQ™ (Compaq Computer Corporation, Houston, Tex.) can be used to store and retrieve patient database information. The PDA or PPC can be a simple stand-alone device that is not networked to other computers, provided the device has a form of data storage, for example solid-state memory, SD (secure digital) and MMC (multimedia card) cards. Alternatively, the PDA or PPC can be attached to a network in which the unit is linked to one or more computers, for example a network server or PC. The networked PDA or PPC can be an intranet system and/or a system linked to computers via the Internet. Thus, the PDA or PPC systems can be Internet attached systems or non-Internet attached systems.

For example, information regarding x-ray images and the parameters that were used to acquire the x-ray image (e.g., acquisition parameters) can be transmitted with the image over a local or long-distance network. The image acquisition parameters can be transmitted simultaneous with the image or before or after the image transmission over the network. Image acquisition parameters that can be transmitted in this fashion include but are not limited to x-ray tube voltage settings, energy settings, x-ray tube current, film-focus distance, object-film distance, collimation, focal spot, spatial resolution, filter settings, etc. These parameters can be entered manually into a data registration sheet or database that can be transmitted before, after or simultaneous with the x-ray images. Alternatively, at least some of these parameters can be transmitted automatically, while others that may be kept constant between different patients can be stored either at the local site or on the network.

Thus, transmission of the x-ray acquisition parameters before, after or simultaneous with the x-ray image over the network can be used to improve the accuracy of quantitative measurements from x-ray images. For example, information on the density of an anatomic structure or a non-living object included on the x-ray image can be derived more accurately, when the x-ray image acquisition parameters are known.

The software can be installed in a PC, a Silicon Graphics, Inc. (SGI) computer or a Macintosh computer.

B. Stand-alone System

Connection to a central network (e.g., the Internet) can be made either directly, or via serial interface adapter. For example, a direct connection could be made if the readout device had wireless capability; alternately, a connection through a SIA or other sort of docking station between the device and the network.

In some instances, a computer system includes a computer having an Intel® Pentium® microprocessor (Intel Corporation, Santa Clara, Calif.) that runs the Microsoft® WINDOWS® Version 3.1, WINDOWS95®, WINDOWS98®, or WINDOWS2000® operating system (Microsoft Corporation, Redmond, Wash.). Of course other microprocessors such as the ATHLON™ microprocessor (Advanced Micro Devices, Inc., Sunnyvale, Calif.) and the Intel® CELERON® and XEON® microprocessors can be utilized. The methods and systems can also include other operating systems, for example, UNIX, LINUX, Apple MAC OS 9 and OS X (Apple, Cupertino, Calif.), PalmOS® (Palm Inc., Santa Clara, Calif.), Windows® CE 2.0 or Windows® CE Professional (Microsoft Corporation, Redmond, Wash.) without departing from the scope of the present invention. Also typically included is the storage media, for example disk drive, removable disk storage, CD-ROM, required to store and retrieve patient database information.

Communication with a computer system can be achieved using a standard computer interface, for example a serial interface or Universal Serial Bus (USB) port. Standard wireless interfaces, for example radio frequency (RF) technology—IEEE 802.11 and Bluetooth, and/or infrared technologies can also be used. The data can be encoded in the standard manner, for example American Standard Code for Information Interchange (ASCII) format—a standard seven-bit code that was proposed by ANSI in 1963, and finalized in 1968. ASCII is the common code for microcomputer equipment.

The computer system can store the information, for example into a database, using a wide variety of existing software that provides a means for inputting data points, and associating the data points with data attributes. Available systems for generating databases and manipulating the resulting databases include but are not limited to Excel® (Microsoft® Corporation, Seattle, Wash.) spreadsheet software, Quattro® (Corel Inc., Ottawa, Canada), Sybase® (Sybase Systems, Emeryville, Calif.), Oracle® (Oracle Inc., Redwood Shores, Calif.), and Sagent Design Studio® (Sagent Technologies Inc., Mountain View, Calif.) systems software. Further, statistical packages and systems for data analysis and data mining are also available (see above). Illustrative examples include but are not limited to SAS® (SAS Institute Inc., Cary, N.C.) and SPSS® (SPSS Inc., Chicago, Ill.). The database can be recorded on, for example a disk drive—internal or external to the system, a Read/Write CD-ROM drive, a tape storage system, solid-state memory or bubble memory, an SD or MMC. In addition to saving the data in a database, the information can be forwarded to an auxiliary readout device such as a display monitor.

C. Networked System

Networked computer systems are also suitable for performing the methods of the present invention. A number of network systems can be used, for example a local area network (LAN) or a wide area network (WAN). The network computer system includes the necessary functionality for forwarding the data in established formats, for example Ethernet or Token Ring Packets or Frames, HTML-formatted data, or WAN digital or analog protocols, in combination with any parameter information, for example Destination Address, or Cyclic Redundancy Check (CRC). CRC is a powerful and easily implemented technique to obtain data reliability. The CRC technique is used to protect blocks of data called Frames. Using this technique, the transmitter appends an extra n-bit sequence to every frame called Frame Check Sequence (FCS). The FCS holds redundant information about the frame that helps the transmitter detect errors in the frame. The CRC is one of the most used techniques for error detection in data communications into a format suitable for transmission across a transmission line for delivery to a database server. Further, the network system may comprises the necessary software and hardware to receive the data from the readout device, store the data, process the data, display the data in a variety of ways, and communicate back to the readout device as well as to allow communication among a variety of users and between these users to the readout device.

The networked computer system, for example an Ethernet, Token Ring or FDDI network, can be accessed using a standard network interface card (NIC), for example a 3Com® EtherLink® NIC (3Com, Inc, Santa Clara, Calif.) which provide network connections over UTP, coaxial, or fiber-optic cabling or an Intel® PRO/100 S Desktop Adapter (Intel Corporation, Santa Clara, Calif.) or using a standard remote access technology, for example a modem using a plain old telephone system (POTS) line, or a xDSL router connected to a digital subscriber lines (DSL), or a cable modem. Additionally, the networked computer system can be connected to the LAN using a standard wireless interface, for example radio frequency (RF) technology—IEEE 802.11 and Bluetooth.

The networked computer system would have the same capability of storing data, as the stand-alone system, onto a storage media, for example a disk drive, tape storage, or CD-ROM. Alternatively, the networked computer system would be able to transfer data to any device connected to the networked computer system for example a medical doctor or medical care facility using standard e-mail software, a central database using database query and update software (e.g., a data warehouse of data points, derived data, and data attributes obtained from a large number of subjects). Alternatively, a user could access from a doctor's office or medical facility, using any computer system with Internet access, to review historical data that may be useful for determining treatment.

If the networked computer system includes a World Wide Web application, the application includes the executable code required to generate database language statements, for example, SQL statements. Such executables typically include embedded SQL statements. The application further includes a configuration file that contains pointers and addresses to the various software entities that are located on the database server in addition to the different external and internal databases that are accessed in response to a user request. The configuration file also directs requests for database server resources to the appropriate hardware, as may be necessary if the database server is distributed over two or more different computers.

Usually each networked computer system includes a World Wide Web browser that provides a user interface to the networked database server. The networked computer system is able to construct search requests for retrieving information from a database via a Web browser. With access to a Web browser users can typically point and click to user interface elements such as buttons, pull down menus, and other graphical user interface elements to prepare and submit a query that extracts the relevant information from the database. Requests formulated in this manner are subsequently transmitted to the Web application that formats the requests to produce a query that can be used to extract the relevant information from the database.

When Web-based applications are utilized, the Web application accesses data from a database by constructing a query in a database language such as Sybase or Oracle SQL which is then transferred to a relational database management system that in turn processes the query to obtain the pertinent information from the database.

Accordingly, in one aspect the present invention describes a method of providing data on x-ray images on a network, for example the Internet, and methods of using this connection to provide real-time and delayed data analysis. The central network can also allow access by the physician to a subject's data. Similarly, an alert could be sent to the physician if a subject's readings are out of a predetermined range, etc. The physician can then send advice back to the patient via e-mail or a message on a web page interface. Further, access to the entire database of data from all subjects may be useful to the for statistical or research purposes. Appropriate network security features (e.g., for data transfer, inquiries, device updates, etc.) are of course employed.

Further, a remote computer can be used to analyze the x-ray that has been transmitted over the network automatically. For example, x-ray density information or structural information about an object can be generated in this fashion. X-ray density information can, for example, be bone mineral density. If used in this fashion, the test can be used to diagnose osteoporosis (See, FIG. 1).

D. Graphical User Interface

In certain of the computer systems, an interface such as an interface screen that includes a suite of functions is included to enable users to easily access the information they seek from the methods and databases of the invention. Such interfaces usually include a main menu page from which a user can initiate a variety of different types of analyses. For example, the main menu page for the databases generally include buttons for accessing certain types of information, including, but not limited to, project information, inter-project comparisons, times of day, events, dates, times, ranges of values, etc.

E. Computer Program Products

A variety of computer program products can be utilized for conducting the various methods and analyses disclosed herein. In general, the computer program products comprise a computer-readable medium and the code necessary to perform the methods set forth supra. The computer-readable medium on which the program instructions are encoded can be any of a variety of known medium types, including, but not limited to, microprocessors, floppy disks, hard drives, ZIP drives, WORM drives, magnetic tape and optical medium such as CD-ROMs.

For example, once an x-ray is transmitted via a local or long-distance computer network and the data on the x-ray received by a remote computer or a computer connected to the remote network computer, an analysis of the morphology of the object can be performed, for example using suitable computer programs. This analysis of the object's morphology can occur in two-dimensions, although it is also possible in three-dimensions, in particular when x-ray images have been acquired through the anatomic object using multiple different x-ray transmission angles. For example, in imaging osseous structures, such morphological analysis of the transmitted x-ray image can be used to measure parameters that are indicative or suggestive of bone loss or metabolic bone disease. Such parameters include all current and future parameters that can be used to evaluate osseous structures. For example, such parameters include, but are not limited to, trabecular spacing, trabecular thickness and intertrabecular space.

Information on the morphology or 2D or 3D morphology of an anatomic structure can be derived more accurately, when x-ray image acquisition parameters such as spatial resolution are known. Other parameters such as the degree of cone beam distortion can also be helpful in this setting.

As noted above, an x-ray image can be transmitted from a local site into a remote server and the remote server can perform an automated analysis of the x-ray. Further, the remote server or a computer connected to the remote server can then generate a diagnostic report. Thus, in certain embodiments, a computer program (e.g., on the remote server or on a computer connected to the remote server) can generate charges for the diagnostic report. The remote server can then transmit the diagnostic report to a physician, typically the physician who ordered the test or who manages the patient. The diagnostic report can also be transmitted to third parties, e.g. health insurance companies. Such transmission of the diagnostic report can occur electronically (e.g. via e-mail), via mail, fax or other means of communication. All or some of the transmitted information (e.g., patient identifying information) can be encrypted to preserve confidentiality of medical records.

Typically, one or more computer programs capable of generating bills will also be employed, for example a bill-making program on the remote server. The charges on the bill will typically follow general medical reimbursement guidelines. The bill can be transmitted electronically (e.g. via e-mail), via mail, fax or other means of communication. Splitting of fees can also be performed by these programs, for example where a percentage of the fee for the diagnostic test is transferred to the physician responsible for interpreting the test, a percentage of the fee for the diagnostic test is transferred to the agency, e.g. a hospital, x-ray clinic, women's clinic, dentist's office acquiring the x-ray image, and a percentage of the fee for the diagnostic test is transferred to the entity responsible for the extraction of x-ray information and automated analysis. Such fees can contain a professional and a technical component. Bills can be transmitted simultaneously with the transmission of the results of the automated network based analysis or can be transmitted after the report is sent. Similarly, payment can be collected using any suitable medium, for example payment by credit card over the Internet or by mail.

Calibration Phantoms

Although a wealth of information can be obtained from x-ray images alone, it is highly preferred that the networked x-ray images include accurate reference markers, for example calibration phantoms for assessing bone mineral density of any given x-ray image. Thus, in certain aspects, the current invention provides for methods and devices that allow accurate quantitative assessment of information contained in an x-ray such as x-ray density of an anatomic structure or morphology of an anatomic structure in a network environment.

An x-ray image can be acquired using well-known techniques from any local site. For example, in certain aspects, 2D planar x-ray imaging techniques are used. 2D planar x-ray imaging is a method that generates an image by transmitting an x-ray beam through a body or structure or material and by measuring the x-ray attenuation on the other side of said body or said structure or said material. 2D planar x-ray imaging is distinguishable from cross-sectional imaging techniques such as computed tomography or magnetic resonance imaging. If the x-ray image was captured using conventional x-ray film, the x-ray can be digitized using any suitable scanning device. The digitized x-ray image is then transmitted over the network, e.g. the Internet, into a remote computer or server. It will be readily apparent that x-ray images can also be acquired using digital acquisition techniques, e.g. using phosphorus plate systems or selenium or silicon detector systems, the x-ray image information is already available in digital format. In this case the image can be transmitted directly over the network, e.g. the Internet, or alternatively, it can be compressed prior to transmission.

In preferred embodiments, when an x-ray of an anatomic structure or a non-living object is acquired a calibration phantom is included in the field of view. Any suitable calibration phantom can be used, for example, one that comprises aluminum or other radio-opaque materials. U.S. Pat. No. 5,335,260 describes other calibration phantoms suitable for use in assessing bone mineral density in x-ray images. Examples of other suitable calibration reference materials can be fluid or fluid-like materials, for example, one or more chambers filled with varying concentrations of calcium chloride or the like. In a preferred embodiment, the material of the phantom is stainless steel (e.g., AISI grade 316 comprising carbon (0.08%); manganese (2%); silicon (1%); phosphorus (0.045%); sulphur (0.03%); nickel (10–14%); chromium (16–18%); molybdenum (2–3%); plus iron to make up 100%). The relative percentages of the components may be with respect to weight or volume.

It will be readily apparent that a calibration phantom can contain several different areas of different radio-opacity. For example, the calibration phantom can have a step-like design, whereby changes in local thickness of the wedge result in differences in radio-opacity. Stepwedges using material of varying thickness are frequently used in radiology for quality control testing of x-ray beam properties. By varying the thickness of the steps, the intensity and spectral content of the x-ray beam in the projection image can be varied. Stepwedges are commonly made of aluminum, copper and other convenient and homogeneous materials of known x-ray attenuation properties. Stepwedge-like phantoms can also contain calcium phosphate powder or calcium phosphate powder in molten paraffin.

FIG. 10 shows an exemplary step-wedge calibration phantom according to the present invention. Panel (A) shows a top view and the overall dimensions. The phantom shown is approximately 2 cm long and 4 mm wide. Each rectangle of the step-wedge is approximately 3 mm long. Panel (B) shows the side view of the step-wedge calibration phantom. The dimensions (e.g., height) of the of each component of the step-wedge is shown between the arrows, as measured in microns. One of skill in the art will recognize that the shape and specific dimensions of the phantom shown in FIG. 10 are exemplary only and can be varied according to the teachings herein. For instances in which the calibration phantom is to be used in small x-rays (e.g., dental x-rays), it is preferable that the overall device be no larger than about 5 cm by 1 cm (or any value therebetween), preferably 3 cm by about 1–50 mm (or any value therebetween), and even more preferably about 2 cm by about 1–5 mm(or any value therebetween).

Alternatively, the calibration reference may be designed such that the change in radio-opacity is from periphery to center (for example in a round, ellipsoid, rectangular of other shaped structure). As noted above, the calibration reference can also be constructed as plurality of separate chambers, for example fluid filled chambers, each including a specific concentration of a reference fluid (e.g., calcium chloride).

Whatever the overall shape of the calibration phantom, it is preferred that at least one marker be present at a known density in the phantom. Presently, areas of the calibration phantom will often fail to appear on x-ray images. This is particularly true of areas at the highest and lowest density levels. Thus, it is often difficult to determine what the density is of any particular area of the calibration phantom. The present invention solves this problem by ensuring that at least one geometric shape is included in the calibration phantom at a position of known density. Any shape can be used including, but not limited to, squares, circles, ovals, rectangles, stars, crescents, multiple-sided objects (e.g., octagons), irregular shapes or the like, so long as their position is known to correlate with a particular density of the calibration phantom. In preferred embodiments, the calibration phantoms described herein are used in 2D planar x-ray imaging.

Since the density and attenuation of the calibration phantom are both known, the calibration phantom provides an external reference for measuring the density of the anatomic structure or non-living object to be measured.

For example, a wedge-shaped calibration phantom can provide reference measurements to express the density of an anatomic structure in terms of thickness of the phantom material. For this purpose, a calibration curve describing the relationship between measured attenuation and material thickness can be derived from the image of the phantom. For a wedge-shaped calibration phantom with the length L and a linear change from a maximum thickness T to thickness 0, each point X in the image of the wedge at distance D from the thin end of the wedge results in a point (T*L/D, G) of the calibration curve, where T*L/D is the thickness of the wedge at X and G the attenuation at X.

A calibration wedge that results in a non-linear calibration curve can be used if the radiograph has to be acquired such that both ends of the wedge cannot be properly identified, so that the distance D is unknown. If the shape of the expected entire calibration curve is known, the part of the curve that can be calculated from the identified regions of the calibration wedge can be fitted to the expected curve. This way, the exact position on the wedge can be determined.

For a known attenuation of a particular anatomic structure, the corresponding thickness value is determined with use of said calibration curve.

Furthermore, calibration curves for measurement units A and B that are calculated with use of the same calibration phantom can be used to translate a measurement from unit A into unit B. For example, bone mineral density can be assessed from a radiograph that also contains an image of an aluminum step wedge. Bone mineral density, which can then be expressed in units of aluminum thickness. In order to translate this into units of calcium concentration, another calibration curve relating units of calcium concentration to aluminum thickness can be created from another radiographic image that contains the same aluminum step wedge as well as samples of varying calcium concentration. Using this second calibration curve, values expressed in aluminum thickness can be converted into units of calcium concentration. One of skill in the art will easily recognize other applications for use of calibration phantoms in x-ray imaging in view of the teachings herein.

The calibration phantoms can be imaged before or after the x-ray image is taken. Alternatively, the calibration phantom can be imaged at the same time as the x-ray image. The calibration phantom can be physically connected to an x-ray film and/or film holder. Such physical connection can be achieved using any suitable mechanical or other attachment mechanism, including but not limited to adhesive, a chemical bond, use of screws or nails, welding, a Velcro™ strap or Velcro™ material and the like. Similarly, a calibration phantom can be physically connected to a detector system or a storage plate for digital x-ray imaging using one or more attachment mechanisms (e.g., a mechanical connection device, a Velcro™ strap or other Velcro™ material, a chemical bond, use of screws or nails, welding and an adhesive).

The attachment may be permanent or temporary and the calibration phantom can be integral (e.g., built-in) to the film, film holder and/or detector system or can be attached or positioned permanently or temporarily appropriately after the film and/or film holder is produced. Thus, the calibration phantom can be designed for single-use (e.g., disposable) or for multiple uses with different x-ray images. Thus, in certain embodiments, the calibration phantom is reusable and, additionally, can be sterilized between uses. Integration of a calibration phantom can be achieved by including a material of known x-ray density between two of the physical layers of the x-ray film. Integration can also be achieved by including a material of known x-ray density within one of the physical layers of the x-ray film. Additionally, the calibration phantom can be integrated into the film cover. A calibration phantom or an external standard can also be integrated into a detector system or a storage plate for digital x-ray imaging. For example, integration can be achieved by including a material of known x-ray density between two of the physical layers of the detector system or the storage plate. Integration can also be achieved by including a material of know x-ray density within one of the physical layers of the detector system or the storage plate.

In certain embodiments, for example those embodiments in which the calibration phantom is temporarily attached to the x-ray assembly, cross-hairs, lines or other markers may be placed on the apparatus as indicators for positioning of the calibration phantom. These indicators can help to ensure that the calibration phantom is positioned such that it doesn't project on materials that will alter the apparent density in the resulting image.

FIG. 2 and FIG. 3 show two examples of dental x-ray film holders that can be designed to include a calibration phantom. (See, also U.S. Pat. No. 5,001,738 and U.S. Pat. No. 4,251,732). It should be noted that FIG. 2 and FIG. 3 depict only two shapes of any number of shapes suitable for x-ray film holders. Furthermore, although illustrated with respect to dental x-ray film and/or film holders, it will be readily apparent that calibration phantoms as described herein can be included in any type of x-ray film and/or film holder.

FIG. 2 shows a film packet (11) for holding x-ray film. Film packet (11) is within a bite wing film holder (10) that has a bite tab (12) extending perpendicular from the film holder (11). The opening (13) allows alignment on a patient's teeth. As shown, the bite tab (12) has a generally square shape. A curved cutaway portion (20) along one edge can be included to allow better aiming of the x-ray tube. A calibration phantom can be positioned in any suitable location on the holder or film following the teachings described herein. In preferred embodiments, it is highly desirable that the calibration phantom be positioned so it doesn't project on structures or materials that will alter the apparent density of the calibration phantoms. It is also desirable that the calibration phantom includes a marker (e.g., geometric pattern) at a known density to increase the accuracy of the phantom as an external standard. Accordingly, the calibration phantom can be positioned where the bite wing (12) meets the film holder (11), for example near the bend (18) or along the area (8) created where the bite wing (12) meets the film holder (11). Such careful positioning ensures that the calibration phantom will appear in the x-ray image between the teeth and, therefore, will be more accurate than if bone (e.g., jaw) or teeth. It will be readily apparent that the area containing the calibration phantom can be made slightly thicker to ensure that the calibration phantom does not project on bone tissue in the x-ray image.

Referring now to FIG. 3, another exemplary x-ray film holder (10) consists of one-piece construction with an extension (2) for alignment of the x-ray beam, and manual positioning of a bite platform (14) and film holding slotted portions (16), (48) and (20). The extension (2) is connected to platform (14) at a 'T' shaped area (22). Film holding slotted portion (16) is perpendicularly connected to platform (14) at (24) and comprises side walls (26) and slot (36) which are used to support film (30), for example in the upper right posterior exposure position as shown in FIG. 3. A calibration phantom (e.g., stepwedge, fluid chambers, etc.) can again be permanently or temporarily positioned in any suitable location, preferably so that it appears in the x-ray image but does not project on or with materials or structures that will alter the apparent density of the calibration references in the x-ray image. Non-limiting examples of such suitable positions include in film holder portions (16, 48, 20), for example within or on the surface of closed portion (50, 60) of the film holders. Other suitable locations can be readily determined following the teachings of the present specification.

FIG. 4 shows another exemplary embodiment in which a calibration phantom (100) is attached to a dental x-ray film holder (200). The film holder (200) with the film (105) is positioned such that the calibration phantom (100), the teeth (300) and the jaw bone (400) project onto the film.

FIG. 5 shows an embodiment in which the calibration phantom (101) is attached (permanently or temporarily) to the x-ray film (500).

FIG. 6 shows an embodiment in which a calibration phantom (120) integrated into the film cover (600) that protects the film (205) from exposure to light.

FIG. 7 shows an embodiment in which a calibration phantom (150) is integrated into a detector system (77). The calibration phantom can be integrated between individual or rows of detectors, or on top or underneath the detectors using any suitable permanent or temporary attachment means (e.g., velcro, adhesive, etc.).

FIG. 8 shows one example of measurement sites (arrows from 108) in a dental x-ray that can be used as intrinsic standards to calibrate the image. Teeth (301) and bone (42) are also depicted.

FIG. 9 shows another example of measurement sites (arrows from 108) in a dental x-ray that can be used as intrinsic standards to calibrate the image. Teeth (320) and bone (410) are also depicted.

Any of the calibration phantom-containing assemblies described herein can be used in methods of analyzing and/or quantifying bone mineral density in an x-ray image. The methods generally involve simultaneously imaging or scanning the calibration phantom and another material (e.g., bone tissue from a subject) for the purpose of quantifying the density of the imaged material (e.g., bone mass). A "subject" preferably refers to an animal, for example a mammal such as a human. As used herein the term "patient" refers to a human subject.

Thus, under the method of the present invention, the calibration phantom is preferably imaged or scanned simultaneously with the individual subject, although the invention allows for non-simultaneous scanning of the phantom and the subject. Methods of scanning and imaging structures by radiographic technique are well known. By placing the calibration phantom in the x-ray beam with the subject, reference calibration samples allow corrections and calibration of the absorption properties of bone. When the phantom is imaged or scanned simultaneously with each subject, the variation in x-ray beam energy and beam hardening are corrected since the phantom and the subject both see the same x-ray beam spectrum. Each subject, having a different size, thickness, muscle-to-fat ratio, and bone content, attenuate the beam differently and thus change the effective x-ray beam spectrum. It is necessary that the bone-equivalent calibration phantom be present in the same beam spectrum as the subject's bone to allow accurate calibration.

X-ray imaging assemblies that are currently in use do not take into account the position of the calibration phantom in relation to the structures being imaged. Thus, when included in known assemblies, calibration phantom(s) are often positioned such that they project on materials or structures (e.g., bone) that alter apparent density of the calibration phantom in the resulting x-ray image. Clearly, this alteration in apparent density will affect the accuracy of the calibration phantom as a reference for determining bone mineral density. Therefore, it is an object of the invention to provide methods in which the calibration phantom projects free of materials or structures that will alter the apparent density of the reference. In the context of dental x-rays, for instance, the methods described herein ensure that the calibration phantom projects free of bone (e.g., teeth, jaw) tissue. As described above with reference to FIGS. 2 and 3, this can be accomplished in a variety of ways, for example, positioning the calibration phantom in the x-ray film or in the x-ray film holder such that it will appear between the teeth in the dental x-ray.

The calibration phantom materials and methods of the present invention are suitable for use in both conventional radiography systems and computed tomography (CT) systems. In conventional radiography systems, for example, a stepwedge phantom can be fabricated from a matrix containing a desired concentration of reference material in varying thicknesses is used. In addition, the calibration phantoms as described herein can readily be configured to be small enough and thin enough to be placed inside the mouth, and the method of the present invention can be used to quantify bone mass using standard dental x-ray systems, for example by including temporary or permanent calibration phantoms in dental x-ray film holders.

In other embodiments of the invention, information inherent in the anatomic structure or the non-living object can be used to estimate the density of selected regions of interest within the anatomic structure or the non-living object. For example, since the x-ray density of muscle, fat, and air are known, the density of air surrounding an anatomic structure or non-living object, the density of subcutaneous fat, and the density of muscle tissue can be used to estimate the density of a selected region of bone, for example within the distal radius.

Said information inherent in said anatomic structure can also be combined with information provided by the calibration phantom. Said combination can result in an improved accuracy of the calibration.

In another embodiment, a general calibration curve is created from a number of reference images that contain a calibration phantom, for example by calculating the average of the calibration curves for the individual reference images. This general calibration curve is then subsequently used to calibrate images that are acquired without a calibration phantom.

The invention also provides kits for obtaining information from x-ray images, for example for obtaining information regarding bone mineral density from an x-ray. In certain embodiments, the kit comprises one or more computer (e.g., software) programs, for example for receiving, analyzing and generating reports based on x-ray images. In further embodiments, the kits can include calibration phantoms, for example calibration phantoms integrated or attachable-to x-ray film and/or x-ray film holders.

All of these aspects of the invention can be practiced separately or in combination. Typically, the use of combinations of the embodiments listed above is more advantageous. Further, although preferred embodiments of the subject invention have been described in some detail, it is understood that obvious variations can be made without departing from the spirit and the scope of the invention.

EXPERIMENTAL

Below are examples of specific embodiments for carrying out the present invention. The examples are offered for illustrative purposes only, and are not intended to limit the scope of the present invention in any way.

EXAMPLE 1

Calibration Phantom Integrated into Film Cover

The workflow presented herein constitutes one example for the use of a calibration phantom with the image acquisition. One skilled in the art will readily recognize other ways to include a calibration phantom in the acquisition process in order to normalize or standardize any form of measurement made from the x-ray image.

In this example, the calibration phantom is integrated into the cover of a dental x-ray film that protects it from exposure to light. The film is placed into the film holder that is used to hold the film in the patient's mouth. The film holder with the film is positioned inside the patient's mouth in such a way that the calibration phantom is not obstructed from the x-ray beam by any structures such as teeth or the lips etc.

After acquisition of the image, the film is taken to the darkroom and the cover with the calibration phantom is removed. The film is then processed in the same way as a conventional dental x-ray film.

EXAMPLE 2

Transmission of X-Ray Image Including Image of Calibration Phantom over a Network This example describes one possible typical application of the invention, in which a digitized x-ray image that includes the image of a calibration phantom is transmitted over a network. Similar applications of the invention can easily be recognized.

The x-ray image is acquired in such a way that the calibration phantom is projected onto the film. The film with the x-ray image and the image of the calibration phantom is developed. Subsequently, the film is digitized, for example using a flat-bed or slide film scanner, resulting in a digital image. The digital image, which includes the x-ray image and the image of the calibration phantom, is then transmitted over a network to a remote computer. The remote computer performs one or more measurements using information from the x-ray image and/or the image of the calibration phantom.

EXAMPLE 3

Transmission of X-Ray Image Including Image Acquisition Parameters

The transmission of image data over a network can also include data describing the image acquisition parameters. After acquisition and digitization of the x-ray image, the acquisition parameters are entered into the local computer system. These parameters can include, but are not limited to, voltage settings, tube current, or film-focus distance. The image and acquisition parameter data are then transmitted over the network to a remote computer.

At the remote computer, the image is analyzed. The acquisition parameters can be used in this evaluation to improve the accuracy of the measurements. The results can be sent back to the original location via a digital network or by fax transmission. The results can also be transmitted to third parties.

EXAMPLE 4

Remote Analysis of X-Ray Image

This example describes a scenario of the invention in which an x-ray image is acquired at a local site and transmitted to a remote site to perform an analysis. Variations of this example can easily be recognized.

After acquisition of the x-ray with a conventional x-ray machine the film is developed. Subsequently, the film is digitized, using, for example, a commercial flat-bed scanner. The digitized image data is transmitted to a remote computer via, for example, a digital network or a phone line. At the remote computer, an automated analysis of the image is performed. The results of this analysis can be sent back to the local computer. They can also be transmitted by a fax connection. The results can also be sent to a third party.

What is claimed is:

1. An x-ray assembly for determining bone mineral density comprising
   an x-ray film cover
   x-ray film and
   a calibration phantom having length (L) and varying thickness (T) along the length and wherein the calibration phantom is attached to the x-ray film cover.
2. The assembly according to claim 1, wherein the calibration phantom projects free of bone tissue.
3. The assembly of claim 1, wherein the calibration phantom is integral to the x-ray film cover.
4. The assembly of claim 1, wherein the x-ray assembly is a dental x-ray assembly.
5. The assembly of claim 1, wherein the thickness of the calibration phantom varies linearly along the length.
6. The assembly of claim 1, wherein the thickness of the calibration phantom varies non-linearly along the length.
7. A method, comprising the steps of
   (a) providing x-ray film, and a calibration phantom having length (L) and varying
   thickness (T) along the length, wherein the thickness of the calibration phantom varies non-linearly along the length;
   (b) producing an x-ray image of an anatomical structure, wherein the x-ray image comprises the calibration phantom;
   (c) providing an expected calibration curve for the non-linear calibration phantom;
   (d) measuring attenuation at a multitude of points in the x-ray image of the calibration phantom; and
   (e) aligning the points measured in step (d) with the expected calibration curve generated in step (c), thereby generating a density calibration curve for the image.
8. The method of claim 7, further comprising the step of translating the calibration curve describing thickness into a curve describing calcium concentration.
9. The method of claim 8, wherein the calibration phantom comprises aluminum and the calibration curve describes aluminum thickness.
10. The method of claim 8, further comprising:
    (a) comparing attenuation information obtained from the x-ray image of a subject's anatomical structure to the generated calibration curve; and
    (b) determining bone mineral density or structure of the subject.
11. The method of claim 7, further comprising the step of calculating the average of calibration curves to generate a reference calibration curve.
12. The method of claim 11, further comprising:
    (a) comparing attenuation information obtained from the x-ray image of a subject's anatomical structure to the generated calibration curve; and
    (b) determining bone mineral density or structure of the subject.
13. The method of claim 7, further comprising:
    (a) comparing attenuation information obtained from the x-ray image of a subject's anatomical structure to the generated calibration curve; and
    (b) determining bone mineral density or structure of the subject.
14. The method of claim 7, wherein the x-ray image is a dental x-ray.
15. The method of claim 7, wherein the calibration curve is generated in a network environment.
16. A method, comprising:
    producing a set of x-ray images, wherein the x-ray images include a calibration phantom having length (L) and varying thickness (T) along the length;

measuring attenuation at a multitude of points in the x-ray images of the calibration phantom, wherein each point is at known distance from a selected part of the phantom;

generating density calibration curves that describes the relationship between measured attenuation and material thickness; and calculating the average of the density calibration curves to generate a reference calibration curve.

17. The method of claim 16, further comprising:
(a) comparing attenuation information obtained from the x-ray image a subject's anatomical structure to the generated calibration curve; and
(b) determining bone mineral density or structure of the subject.

18. The method of claim 16, further comprising providing an x-ray film holder attached to the calibration phantom and x-ray film.

19. The method of claim 16, further comprising
producing an x-ray image without the calibration phantom of an anatomical structure; and
calibrating the x-ray image without the calibration phantom using the reference calibration curve.

20. The method of claim 16, wherein the set of x-ray images are of the same anatomical structure in different individuals.

21. A method of generating a density calibration curve, comprising the steps of
(a) generating a digital x-ray image of an anatomic structure that includes a wedge-shaped calibration phantom having length (L) and varying thickness (T) along the length;
(b) generating an expected calibration curve for the wedge-shaped calibration phantom; and
(c) measuring attenuation at a multitude of points in the x-ray image including the calibration phantom;
(d) aligning the points measured in step (c) with the expected calibration curve generated in step (b), thereby generating a calibration curve for the image.

22. The method of claim 21, further comprising the step of translating the calibration curve describing thickness into a curve describing calcium concentration.

23. The method of claim 22, wherein the calibration phantom comprises aluminum and the calibration curve describes aluminum thickness.

24. A kit comprising an x-ray film cover, x-ray film, a calibration phantom attached to the x-ray film cover, an x-ray imaging assembly and computer programs, wherein said computer programs analyze and assess bone mineral density.

25. A method comprising the step of analyzing an x-ray image obtained using an x-ray film cover, x-ray film, and a calibration phantom having length (L) and varying thickness (T) along the length;

comparing a bone mineral density to a reference standard;

making a diagnosis of osteoporosis if the bone mineral density is below the reference standard.

26. The method of claim 25, further comprising administering one or more anti-resorptive agents or one or more anabolic agents.

27. A calibration phantom comprising a plurality of geometric shapes, wherein a first shape of the plurality of geometric shapes is of a first geometric type, and a second shape of the plurality of geometric shapes is of a second geometric type different from the first geometric type.

28. The calibration phantom according to claim 27, wherein the first type is rectanguler and forms a step-wedge.

29. The calibration phantom according to claim 27, wherein the phantom comprises stainless steel.

30. The calibration phantom according to claim 29, wherein the stainless steel comprises 0.08% carbon, 2% manganese, 1% silicon, 0.045% phosphorus, 0.03% sulphur; 10–14% nickel, 16–18% chromium, 2–3% molybdenum and 61.845%–68.845% iron.

31. The calibration phantom of claim 27, wherein the calibration phantom is less than 2.5 cm in length and less than 5 mm in width.

32. The calibration phantom of claim 27, wherein each geometric shape comprises at least one material in common.

33. An x-ray assembly for determining bone mineral density comprising
an x-ray film cover;
x-ray film and
a calibration phantom having length (L) and varying thickness (T) along the length and wherein the calibration phantom is integrated into the film.

34. The assembly according to claim 33, wherein the calibration phantom projects free of bone tissue.

35. The assembly of claim 33, wherein the x-ray assembly is a dental x-ray assembly.

36. The assembly of claim 33, wherein the thickness of the calibration phantom varies linearly along the length.

37. The assembly of claim 33, wherein the thickness of the calibration phantom varies non-linearly along the length.

* * * * *

UNITED STATES PATENT AND TRADEMARK OFFICE
CERTIFICATE OF CORRECTION

| | | |
|---|---|---|
| PATENT NO. | : 7,050,534 B2 | Page 1 of 1 |
| APPLICATION NO. | : 10/225363 | |
| DATED | : May 23, 2006 | |
| INVENTOR(S) | : Philipp Lang | |

It is certified that error appears in the above-identified patent and that said Letters Patent is hereby corrected as shown below:

Column 1, line 5, prior to "CROSS REFERENCE TO RELATED APPLICATIONS", insert the following text:
-- STATEMENT AS TO RIGHTS TO INVENTIONS MADE UNDER FEDERALLY SPONSORED RESEARCH AND DEVELOPMENT
Certain aspects of the invention described below were made with United States Government support under Advanced Technology Program 70NANB2H3007 awarded by the National Institute of Standards and Technology (NIST). The United States Government may have rights in certain of the inventions. --

Signed and Sealed this

Thirteenth Day of May, 2008

JON W. DUDAS
*Director of the United States Patent and Trademark Office*